United States Patent [19]

Baba et al.

[11] 4,010,149
[45] Mar. 1, 1977

[54] ANALOGS OF LH-RH AND PROCESS FOR PREPARING THE SAME

[75] Inventors: Yoshihiko Baba; Yutaka Okada; Hiroyashi Horikoshi; Yuichiro Yabe, all of Tokyo, Japan

[73] Assignee: Sankyo Company Limited, Tokyo, Japan

[22] Filed: Apr. 7, 1975

[21] Appl. No.: 565,362

[30] Foreign Application Priority Data

Apr. 26, 1974 Japan .............................. 49-48174

[52] U.S. Cl. ...................... 260/112.5 LH; 424/177
[51] Int. Cl.² .................. C07C 103/52; C07G 7/00
[58] Field of Search .......................... 260/112.5 LH

[56] References Cited
UNITED STATES PATENTS

| | | | |
|---|---|---|---|
| 3,855,199 | 12/1974 | Foell et al. ............... | 260/112.5 LH |
| 3,886,137 | 5/1975 | Yardley ................... | 260/112.5 LH |

OTHER PUBLICATIONS

Fujino et al. Biochem. Biophys. Res. Comm., 57, 1248–1256 (1974).

*Primary Examiner*—Lewis Gotts
*Assistant Examiner*—Reginald J. Suyat
*Attorney, Agent, or Firm*—Toren, McGeady and Stanger

[57] ABSTRACT

Peptides having the formula
N-Acetyl-N-methylglycyl-L-histidyl-L-tryptophyl-L-seryl-L-tyrosyl-Y-L-leucyl-L-arginyl-L-prolyl-Z
wherein Y is a D-α-alkylglycine residue of the formula

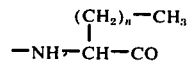

in which $n$ is an integer of 0 through 3 inclusive and Z is ethylamino group or an ethylamino group which is substituted with 1 to 3 fluorine atoms at the 2-position and pharmaceutically acceptable salts thereof. They show luteinizing hormone-releasing hormone like activities and are prepared by reacting L-histidyl-L-tryptophyl-L-seryl(or L-seryl having a protected hydroxyl group)-L-tyrosyl(or L-tyrosyl having a protected hydroxyl group)-Y-L-leucyl-L-arginyl(or L-arginyl having a protected guanidyl group)-L-prolyl-Z wherein Y and Z are as defined above with a reactive derivative of N-Acetyl-N-methylglycine and, if a protective group is attached, then removing the protective group, and, if necessary, converting further the resultant into an acid addition salt thereof in the usual manner.

8 Claims, 2 Drawing Figures

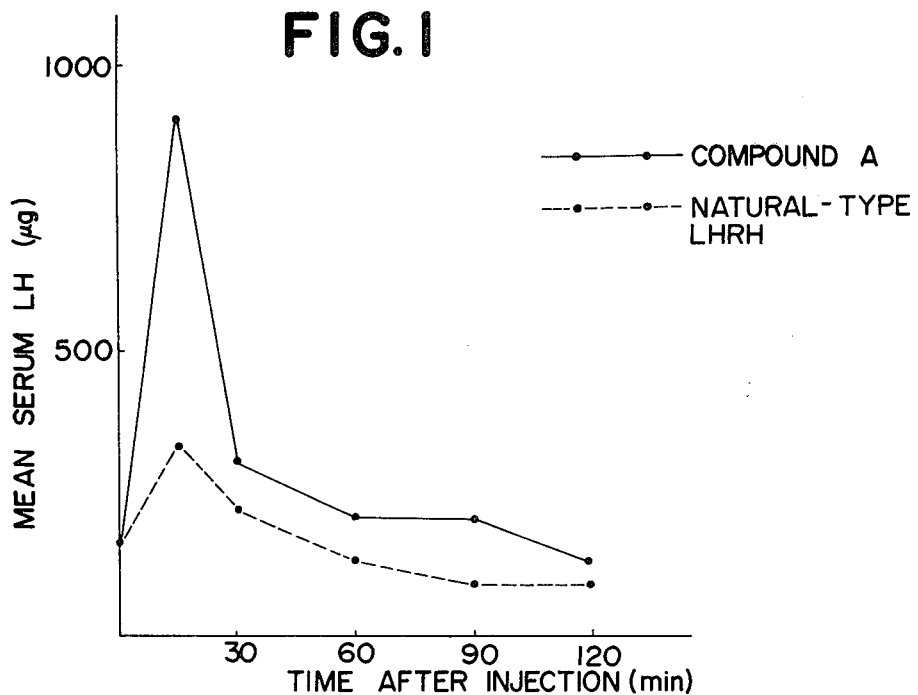
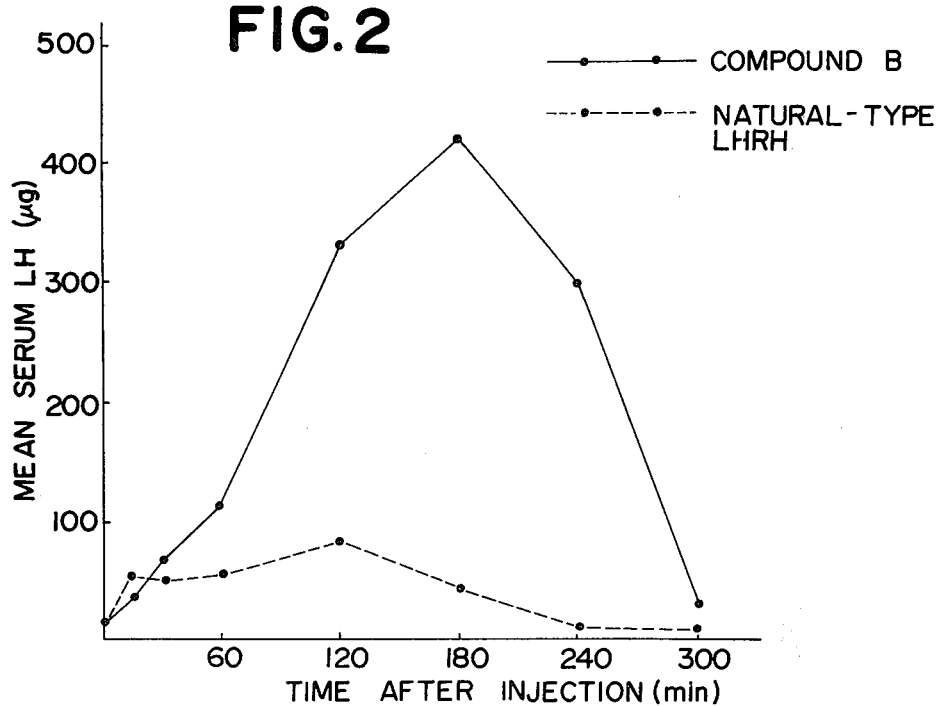

ANALOGS OF LH-RH AND PROCESS FOR PREPARING THE SAME

This invention relates to a new class of peptides and a process for preparing the same.

More particularly, it is concerned with a peptide having the formula

N-acetyl-N-methylglycyl-L-histidyl-L-tryptophyl-L-seryl-L-tyrosyl-Y-L-leucyl-L-arginyl-L-prolyl-Z ... (I)

wherein Y is a D-α-alkylglycine residue of the formula

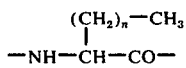

in which $n$ is an integer of 0 through 3 inclusive and Z is ethylamino group or an ethylamino group which is substituted with 1 to 3 fluorine atoms at the 2-position and a pharmaceutically acceptable salt thereof as well as a process for the preparation of the same.

In the above formula (I), Y may be exemplified by D-alanine or D-norleucine residue and Z may be exemplified by ethylamino, β-fluoroethylamino, 2,2-difluoroethylamino or 2,2,2-trifluoroethylamino group.

The new peptides of this invention have been found to show a prominent activity like Luteinizing Hormone-Releasing Hormone (hereinafter referred to frequently as "LH-RH") which is known to be one of Hypothalamus releasing hormones. Where the present peptide is to be administered to human being, the dosage to be given may vary depending mainly upon the age, body weight, condition and other factors of the subject. In general, a single dose from 1 μg to 500 μg, preferably 10 μg to 100 μg, is employable for an adult. Parenteral administration, particularly, hypodermic injection, endodermic injection, intramuscular injection etc. may be practically preferable.

Since the amino acid sequence of natural LH-RH was identified as L-pyroglutamyl-L-histidyl-L-tryptophyl-L-seryl-L-tyrosylglycyl-L-leucyl-L-arginyl-L-prolylglycine amide [Science, 173, 1036 (1971)], there have been prepared many analogous compounds. Of these compounds, the analogous compound in which the glycine of the sixth amino acid is replaced with D-alanine and the nonapeptide compound in which the glycine of the tenth amino acid is replaced with ethylamine or n-propylamine have been reported to have physiological activity superior to the natural LH-RH [according to The Endocrine Society (USA), the 55th annual meeting held at Chicago, USA, in June, 1973 and Biochemical and Biophysical Research Communications, 49, 863 (1972)].

As a result of our studies on peptide showing LH-RH like activities, we have found that the present peptides (I) in which the N-terminal group (L-pyroglutamic acid residue), the glycine residue at the 6-position and the C-terminal group (glycineamide group) are replaced with other groups with respect to natural LH-RH, have physiological activities stronger than the natural LH-RH has, and this invention has been completed upon this finding.

It is, accordingly, a primary object of this invention to provide a new group of the peptides which show potent LH-RH-like activities.

Another object of this invention is to provide a process for preparing new peptides (I).

These and other objects and advantages of this invention will be apparent from the following description.

According to one aspect of this invention, there is provided a new class of the peptides having the formula (I) which show a high LH-RH-like activity and pharmaceutically acceptable salts thereof.

Of the peptides (I), a preferable group is composed of those peptides having the formula (I) in which Z is ethylamino group or 2-fluoroethylamino group in view of their physiological activities.

Representative and more preferable peptides of the present ones (I) are illustratively shown below.

Compound No./Chemical Name

1. N-Acetyl-N-methylglycyl-L-histidyl-L-tryptophyl-L-sery-L-tyrosyl-D-alanyl-L-leucyl-L-arginyl-L-prolineethylamide.
2. N-Acetyl-N-methylglycyl-L-histidyl-L-tryptophyl-L-seryl-L-tyrosyl-D-alanyl-L-leucyl-L-arginyl-L-proline-2,2,2-trifluoroethylamide.
3. N-Acetyl-N-methylglycyl-L-histidyl-L-tryptophyl-L-seryl-L-tyrosyl-D-norleucyl-L-leucyl-L-arginyl-L-prolineethylamide.
4. N-Acetyl-N-methylglycyl-L-histidyl-L-tryptophyl-L-seryl-L-tyrosyl-D-norleucyl-L-leucyl-L-arginyl-L-proline-β-fluoroethylamide.
5. N-Acetyl-N-methylglycyl-L-histidyl-L-tryptophyl-L-seryl-L-tyrosyl-D-norleucyl-L-leucyl-L-arginyl-L-proline-2,2,2-trifluoroethylamide.

As explained hereinabove, pharmaceutically acceptable salts of the peptides (I) also show potent LH-RH-like activities.

Preferred acids capable of forming an acid addition salt are those generally used for pharmaceuticals in the form of an acid addition salt and may be exemplified by mineral acids such as hydrochloric acid and sulfuric acid and organic acids such as acetic acid, propionic acid, oxalic acid, malonic acid, succinic acid, citric acid, lactic acid, benzoic acid and tartaric acid.

According to another aspect of this invention, there is provided a process for preparing the peptide (I) which comprises reacting a peptide having the formula L-histidyl-L-tryptophyl-L-seryl (or L-seryl having a protected hydroxyl group)-L-tyrosyl(or L-tyrosyl having a protected hydroxyl group)-Y-L-leucyl-L-arginyl(or L-arginyl having a protected guanidyl group)-L-prolyl-Z ... (II)

wherein Y and Z are as defined above with a reactive derivative of N-acetyl-N-methylglycine ... (III)

and, if a protective group is attached, then removing the protective group, and, if necessary, converting further the resultant into an acid addition salt thereof in the usual manner.

The protective group for functional groups of sidechains of the amino acids constituting the aforementioned compound (II) to be used in the process of the present invention may be protective groups which may be generally employed in known processes for preparing peptides, and there is no other limitation. Usually employable protective groups may be exemplified as follows: benzyl, tert.-butyl, tetrahydropyranyl and the like for the hydroxyl group of the serine; tert.-butyl, acetyl and the like for the hydroxyl group of the tyrosine; and nitro, tosyl, benzyloxycarbonyl and the like for the guanidyl group of the arginine. For removing these protective groups, methods employed generally in known processes for preparing peptides may likewise be employed without any specific limitation. Such methods may be exemplified as follows: hydrolysis of an ester and an ether with an acid or an alkali; reductive removal of benzyl, benzyloxycarbonyl, nitro and tosyl with liquid ammonia-metallic sodium or through catalytic reduction; removal of tert.-butyl, benzyl, benzyloxycarbonyl, nitro and tosyl with hydrogen fluoride. Protective groups most usually employed are as follows: tert.-butyl for the hydroxyl group; and nitro or tosyl for the guanidyl group.

It is desirable to employ the aforementioned compound (II) as early as possible, after preparing by the removal of the protective group from the compound which was previously protected at the N-terminal, inside or outside the present reaction system, before practising the procedure of the process of the present invention. The protective groups for the N-terminal are the protective groups which may be usually employed in the preparation of peptides, and they are exemplified by benzyloxycarbonyl, tert.-butoxycarbonyl, tert.-amyloxycarbonyl, trityl, formyl, tosyl, trifluoroacetyl and the like. However, said exemplified groups are not intended to be limitative. The removal procedure is carried out in the usual manner, for instance, through catalytic reduction, hydrolysis with an acid or alkali, reduction with liquid ammonia-metallic sodium and the like.

The reactive derivatives of the aforementioned compound (III) which may be used in the process of the present invention are reactive groups usually employed in the preparation of peptides, and there is no other limitation on the derivative. For instance, they may be an active ester, an acid azide, an acid halide, a mixed acid anhydride, an acid anhydride and the like. The reactive group may be introduced, if desired, as follows: The compound (III) is caused to react with N,N-dicyclohexylcarbodiimide, carbonyldiimidazole and the like, and with the compound (II) simultaneously or in arbitrary order.

The most preferred reactive derivative is an active ester, and all active esters usually employed in the preparation of peptides may be adopted with no specific limitation. Such active esters may be those of a phenol having electron-attractive substituents on the benzene ring, such as, p-nitrophenylester and polyhalogenophenylester e.g., 2,3,5-trichlorophenylester, pentachlorophenylester and pentafluorophenylester; those of hydroxyquinoline or hydroxypyridine, such as, 8-quinolylester and 2-pyridylester; those of thiophenol; those of N-hydroxyimide such as succinimide ester, phthalimide ester, and the like.

The process of the present invention may be easily carried out by bringing the aforementioned compound (II) into contact with a reactive derivative of the aforementioned compound (III) in an appropriate solvent. There is no specific limitation on the solvent to be used, so far as it does not participate in the present reaction. Such a solvent may preferably be one of various solvents which can highly dissolve the starting compounds, for instance, dimethylformamide, dimethylacetamide and acetonitrile. There is likewise no specific limitation on the reaction temperature. However, in order to avoid side reactions and to obtain the desired compound in a good yield, a relatively low temperature may preferably be adopted, and it may be within $-10°$ C – $-40°$ C, in general. The reaction period may vary depending principally upon nature of the starting compound, the reaction temperature, nature of the solvent and the like, and is between several hours and several tens of hours.

After completion of the reaction, the desired compound is recovered from the reaction mixture in the usual way. For instance, the desired compound may be precipitated by adding to the reaction mixture a solvent which does not dissolve the desired compound. Further, the so obtained compound may be purified according to the conventional method, for instance, gel-filtration, column chromatography and reprecipitation.

The process of the present invention is further concretely illustrated by the following examples. However, the present invention is not limited by the examples.

In the examples, the thin-layer chromatography was conducted by using DC-Fertiplatten Kieselgel 60F254 (thickness, 0.25mm; available from Merck & Co., Inc.). The developing agents were as follows:

I. n-Butanol — acetic acid — water (60:15:25)
II. n-Butanol — pyridine — acetic acid — water (15:10:3:12)
III. Chloroform — methanol — 32% acetic acid (60:45:20)

The desired compounds were detected by utilizing U.V. light irradiation, Ehrlich color reaction, Pauly's color reaction and Sakaguchi color reaction. $R_f$ values of the standard LH-RH in the above-mentioned solvents I, II and III were 0.33, 0.52 and 0.63, respectively.

The amino acid analysis was conducted by means of an automatic analyser, after hydrolysis performed at 110° C for 24 hours with constant boiling point hydrochloric acid (containing 4% thioglycolic acid) in a sealed evacuated tube.

EXAMPLE 1

N-Acetyl-N-methylglycyl-L-histidyl-L-tryptophyl-L-seryl-L-tyrosyl-D-alanyl-L-leucyl-L-arginyl-L-proline ethylamide In 0.5 ml of dry pyridine were dissolved 40 mg of N-acetyl-N-methylglycine (m.p. 139° – 140° C) and 140 mg of p-nitrophenyl trifluoroacetate, and the solution was left at room temperature for 2 hours. Completion of the reaction for the formation of N-acetyl-N-methylglycine p-nitrophenylester was confirmed by means of thin layer chromatography, and then the solvent was distilled off under reduced pressure. To the residue was added 5 ml of water, and extraction was made with ethyl acetate. The extract was repeatedly washed with water until the water portion became neutral. The extract was dried over anhydrous sodium sulfate and evaporated to leave acetyl-N-methylglycine p-nitrophenylester as an oil.

In a mixture of 5 ml of acetic acid, 20 ml of methanol and 10 ml of water was, separately, dissolved 160 mg of $N^\alpha$-benzyloxycarbonyl-L-histidyl-L-tryptophyl-L-seryl-L-tyrosyl-D-alanyl-L-leucyl-L-arginyl-L-prolineethylamide acetate [$R_f$ value on thin layer chromatography: I, 0.52; II, 0.80; III 0.81] and the resulting solution was subjected to catalytic reduction at room temperature for 9 hours in the presence of 100 mg of 10% palladium-carbon catalyst. The catalyst was then removed from the reaction mixture by filtration. The solvent was distilled off under reduced pressure, and then the residue was dried under vacuum. The residue was dissolved in 1 ml of dimethylformamide, and, after addition of the active ester obtained earlier, the mixture was left at room temperature for 15 hours. To the reaction mixture was added 30 ml of ethyl acetate, and the precipitate produced was collected by filtration and washed with ethyl acetate. The precipitate was then dissolved in 3 ml of methanol and reprecipitated by addition of 30 ml of ethyl acetate. The precipitate thus produced was collected by filtration and dried under reduced pressure to give 143 mg of the desired product (crude).

The crude product (50 mg) was then purified by the use of partition chromatography [support: Sephadex G-25, column size: 2.7 × 90 cm, agent: n-butanol — acetic acid — water (4:1:5)]. The fractions of 10 ml each were taken and checked by the use of both UV spectrum (at 280 mμ) and thin layer chromatography for ascertaining fractions which contained the desired product. The fractions of from the 31st to the 35th were then combined and concentrated to dryness under reduced pressure. The residue was dissolved in a small amount of 1% acetic acid and, after addition of a small amount of active carbon, the mixture was shaken and filtered. The filtrate was freeze-dried to give 22.1 mg of the desired compound in the pure acetate form.

Optical rotation: $[\alpha]_D^{20}$ −49.5 (C=0.19, 0.1 N acetic acid)

$R_f$ value on thin layer chromatography: I, 0.37; II, 0.58; III, 0.69.

Amino acid analysis (relative value based on a leucine value of 1):

| Amino acid | Theoretical | Found |
|---|---|---|
| Serine | 1 | 0.83 |
| Proline | 1 | 0.94 |
| Alanine | 1 | 1.06 |
| Leucine | 1 | 1.00 |
| Tyrosine | 1 | 0.99 |
| Tryptophan | 1 | 0.90 |
| Histidine | 1 | 0.99 |
| Arginine | 1 | 0.95 |
| N-Methylglycine | 1 | 0.91 |

EXAMPLE 2

N-Acetyl-N-methylglycyl-L-histidyl-L-tryptophyl-L-seryl-L-tyrosyl-D-alanyl-L-leucyl-L-arginyl-L-proline-2,2,2-trifluoroethylamide 200 mg of $N^\alpha$-benzyloxycarbonyl-L-histidyl-L-tryptophyl-L-seryl-L-tyrosyl-D-alanyl-L-leucyl-L-arginyl-L-proline-2,2,2-trifluoroethylamide [$R_f$ values on thin layer chromatography, I, 0.48; II, 0.73; III, 0.82: Optical rotation, $[\alpha]_D^{17}$ −22° (C=0.3, acetic acid)] was stirred in the presence of 0.15 ml of mercaptoethanol, 0.1 ml of anisole and 5 ml of hydrogen fluoride under ice-cooling for 30 minutes. The hydrogen fluoride was distilled off under reduced pressure and 10 ml of water was added to the residue. The resulting mixture was adjusted to pH 9 with triethylamine, shaken with three portions of 10 ml of ethyl acetate and insolubles were filtered off. The resulting aqueous solution was concentrated to dryness under reduced pressure. The residue was dissolved in 1 ml of dimethylformamide and 20 mg of N-acetyl-N-methylglycine 2,3,5-trichlorophenylester (m.p. 70° − 73° C., needles) was added. The resulting mixture was left for 6 hours at room temperature and then 10 ml of ethyl acetate was added to separate out precipitates which were then collected by centrifugation (2000 r.p.m., 5 minutes) and purified by the use of partition chromatography [support: Sephadex G-25 (trade name), column size 2.7 × 90 cm, agent: n-butanol-acetic acid-water (4:1:5)]. The fractions of 10 ml each were taken and checked by the use of both UV spectrum (at 280 mμ) and thin layer chromatography for ascertaining fractions which contained the desired product. The fractions of from the 55th to the 59th were then combined, concentrated under reduced pressure and dried in vacuum. The residue was dissolved in a small amount of water and subjected to column chromatography [SP-Sephadex C-25 ($NH_4^+$form, trade name; column size 1 × 10 cm]. 50 ml of a 0.02 mole ammonium bicarbonate solution was passed therethrough. By raising the concentrations of the ammonium bicarbonate solution used to 0.06 mole through 0.04 mole, were eluated the desired fractions. These fractions were collected, suction filtered and freeze-dried. The so obtained powdery substance was dissolved in 5 ml of 0.5N acetic acid and again freeze-dried to give the desired compound in the pure acetate form. Yield 43 mg.

Optical rotation: $[\alpha]_D^{20}$ −40.6° (C=0.3, 0.1 N acetic acid)

$R_f$ value on thin layer chromatography: I, 0.36; II, 0.56; III, 0.69.

Amino acid analysis (relative value based on a leucine value of 1):

| Amino acid | Theoretical | Found |
|---|---|---|
| Serine | 1 | 0.86 |
| Proline | 1 | 1.04 |
| Alanine | 1 | 1.02 |
| Leucine | 1 | 1.00 |
| Tyrosine | 1 | 1.03 |
| Tryptophan | 1 | 0.96 |
| Histidine | 1 | 1.02 |
| Arginine | 1 | 1.02 |
| N-Methylglycine | 1 | 0.97 |

EXAMPLE 3

N-Acetyl-N-methylglycyl-L-histidyl-L-tryptophyl-L-seryl-L-tyrosyl-D-norleucyl-L-leucyl-L-arginyl-L-L-prolineethylamide 80 mg of $N^\alpha$-benzyloxycarbonyl-L-histidyl-L-tryptophyl-L-seryl-L-tyrosyl-D-norleucyl-L-leucyl-L-arginyl-L-prolineethylamide [$R_f$ values on thin layer chromatography, I, 0.56; II, 0.75; III, 0.90: Optical rotation, $[\alpha]_D^{17}$ −22° (C=0.3, glacial acetic acid)] was stirred in the presence of 0.15 ml of mercaptoethanol, 0.1 ml of anisol and 5 ml of hydrogen fluoride under ice-cooling for 30 minutes. The hydrogen fluoride was distilled off under reduced pressure, 10 ml of water was added to the residue and the resulting mixture was adjusted to pH 9 with triethylamine. The mixture was washed three times with ethyl acetate and insolubles were removed by centrifugal separation. The resulting aqueous solution was concentrated to dryness under reduced pressure. The residue was dissolved in 1 ml of dimethylformamide and 15 mg of N-acetyl-N-methylglycine 2,3,5-trichlorophenyl ester was added. After standing at room temperature overnight, 10 ml of ethyl acetate was added to separate out precipitates. The precipitates were collected by centrifugal separation (2000 r.p.m., 5 minutes) and subjected to partition chromatography in the same manner as in Example 2. The fractions of from the 29th to the 34th each were taken and subjected to column chromatography in the same manner as in Example 2 and then twice freeze-dried. Yield 31 mg.

Optical rotation: $[\alpha]_D^{17}$ −31.1° (C=0.3, 0.1 N acetic acid)

$R_f$ value on thin layer chromatography: I, 0.40; II, 0.69; III, 0.83.

Amino acid analysis (relative value based on a leucine value of 1):

| Amino acid | Theoretical | Found |
| --- | --- | --- |
| Serine | 1 | 0.85 |
| Proline | 1 | 0.96 |
| Leucine | 1 | 1.00 |
| Norleucine | 1 | 0.98 |
| Tyrosine | 1 | 1.00 |
| Tryptophan | 1 | 0.87 |
| Histidine | 1 | 0.98 |
| Arginine | 1 | 0.97 |
| N-Methylglycine | 1 | 0.88 |

EXAMPLE 4

N-Acetyl-N-methylglycyl-L-histidyl-L-tryptophyl-L-seryl-L-tyrosyl-D-norleucyl-L-leucyl-L-arginyl-L-proline-2-fluoroethylamide In the same manner as in Examples 2 and 3, the desired product was obtained from 50 mg of $N^\alpha$-benzyloxycarbonyl-L-histidyl-L-tryptophyl-L-seryl-L-tyrosyl-D-norleucyl-L-leucyl-L-arginyl-L-proline-β-fluoroethylamide [$R_f$ values on thin layer chromatography, I, 0.56; II, 0.72; III, 0.89: Optical rotation $[\alpha]_D^{17}$ −23.0° (C=0.3, glacial acetic acid)]. Yield 17 mg.

Optical rotation: $[\alpha]_D^{17}$ −29.5° (C=0.3, 0.1 N acetic acid)

$R_f$ value on thin layer chromatography: I, 0.43; II, 0.68; III, 0.83.

Amino acid analysis (relative value based on a leucine value of 1):

| Amino acid | Theoretical | Found |
| --- | --- | --- |
| Serine | 1 | 0.82 |
| Proline | 1 | 1.00 |
| Leucine | 1 | 1.00 |
| Norleucine | 1 | 1.02 |
| Tyrosine | 1 | 1.01 |
| Tryptophan | 1 | 0.82 |
| Histidine | 1 | 0.99 |
| Arginine | 1 | 1.04 |
| N-Methylglycine | 1 | 0.88 |

EXAMPLE 5

N-Acetyl-N-methylglycyl-L-histidyl-L-tryptophyl-L-seryl-L-tyrosyl-D-norleucyl-L-leucyl-L-arginyl-L-proline-2,2,2-trifluoroethylamide In the same manner as in Examples 2, 3 and 4, the desired product was obtained from 50 mg of $N^\alpha$-benzyloxycarbonyl-L-histidyl-L-tryptophyl-L-seryl-L-tyrosyl-D-norleucyl-L-leucyl-L-arginyl-L-proline 2,2,2-trifluoroethylamide [$R_f$ values on thin layer chromatography, I, 0.52; II, 0.75; III, 0.85: Optical rotation $[\alpha]_D^{17}$ −15° (C=0.3, glacial acetic acid)]. Yield 11.1 mg.

Optical rotation: $[\alpha]_D^{17}$ −32.5° (C=0.3, 0.1 N acetic acid)

$R_f$ value on thin layer chromatography: I, 0.39; II, 0.61; III, 0.76.

Amino acid analysis (relative value based on a leucine value of 1):

| Amino acid | Theoretical | Found |
| --- | --- | --- |
| Serine | 1 | 0.80 |
| Proline | 1 | 1.07 |
| Leucine | 1 | 1.00 |
| Norleucine | 1 | 1.03 |
| Tyrosine | 1 | 0.98 |
| Tryptophane | 1 | 0.71 |
| Histidine | 1 | 0.90 |
| Arginine | 1 | 0.98 |
| N-Methylglycine | 1 | 0.98 |

In order to illustrate excellent biological activity of the peptide of this invention, the experiments will be given as follows:

EXPERIMENT 1

Examination of ovulation inducing effect

F. Wistar-Imamichi rats (body weight: around 250 g) were bred at room temperature (23° ±1° C) under an artificial light (on at 5:00 a.m. and off at 7:00 p.m.). Among these rats, the rats which had more than three times of four days sexual cycle were subjected to the test.

At 1:00 p.m. on proestrus days, pentobarbital sodium salt was intraperitoneally administered into each of rats (in the amount of 30 mg/kg). Then, at 4:00 p.m. of the same day, a test sample dissolved in 0.1 ml of isotonic sodium chloride solution was subcutaneously injected. Between noon and 1:00 p.m. of the next day, the rats were sacrificed and the oviduct was immediately taken out. The oviduct was then placed between a couple of slide glasses and examined for ova through a microscope. The test was conducted by employing five rats for a certain dosage of test samples. The results are shown below in the term of $ED_{50}$.

| Test sample | $ED_{50}$ μg/body |
| --- | --- |
| Natural-type LH-RH (synthesized) | 0.134 |
| Compound A[1] | 0.018 |
| Compound B[2] | 0.0125 |

Note:
[1]N-Acetyl-N-methylglycyl-L-histidyl-L-tryptophyl-L-Seryl-L-tyrosyl-D-alanyl-L-leucyl-L-arginyl-
[2]N-Acetyl-N-methylglycyl-L-histidyl-L-tryptophyl-L-seryl-L-tyrosyl-D-norleucyl-L-leucyl-L-arginyl-L-proline-2-fluoroethylaminde It will be apparent from the above results that the peptides of this invention show a much higher ovulation inducing effect than natural-type LH-RH.

EXPERIMENT 2

Determination of serum Luteinizing Hormone (LH) levels after the administration LH-RH and the present peptides I. 2.5 μg each of natural-type LH-RH and the present compound (hereinafter referred to as Compound A), N-acetyl-N-methylglycyl-L-histidyl-L-tryptophyl-L- seryl-L-tyrosyl-D-alanyl-L-leucyl-L-arginyl-L-prolineethylamide, was dissolved in 0.5 ml saline and subcutaneously injected in ovariectomized estrogen-progesterone pretreated rats according to the teachings by V. D. Ramirez et al. in Endocrinology, 73, 193 (1963).

Blood samples were collected from jugular vein 15, 30, 60, 90 and 120 minutes after the injection and, after the separation of serum, the concentrations of serum LH were estimated by radioimmunoassay according to the teachings by G. D. Niswender et al. in the Proc. Soc. Exptl. Biol. Med., 128, 807 (1968).

Serum LH levels of the test compounds are graphically shown in FIG. 1 wherein a serum LH level of the Compound A is represented by a full line and the one of natural-type LH-RH by a dotted line.

II. 50 μg each of natural-type LH-RH and the present compound (hereinafter referred to as Compound B), N-acetyl-N-methylglycyl-L-histidyl-L-tryptophyl-L-seryl-L-tyrosyl-D-norleucyl-L-arginyl-L-proline-2-fluoroethylamide, was dissolved in 0.5 ml saline and subcutaneously injected in the same group of male matured goats at a two week's interval in the same manner as in the above (I).

Blood samples were collected from jugular vein 15, 30, 60, 120, 180, 240 and 300 minutes after the injection and then the concentrations of serum LH were estimated by radioimmunoassay in the same manner as in the above (II).

Serum LH levels of the test compounds are graphically shown in FIG. 2 wherein a serum LH level of the Compound B is represented by a full line and the one of natural-type LH-RH by a dotted line.

It will be apparent from the results shown in FIGS. 1 and 2 that the present peptides can stimulate the release of LH much higher than natural-type LH-RH and that the higher serum LH levels continue markedly longer in the present peptides.

What is claimed is:

1. A peptide having the formula N-Acetyl-N-methylg lycyl-L-histidyl-L-tryptophyl-L-seryl-L-tyrosyl-Y-L-leucyl-L-arginyl-L-prolyl-Z
wherein Y is a D-α-alkylglycine residue of the formula

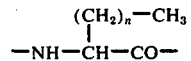

in which n is an integer of 0 through 3 inclusive and Z is ethylamino group or an ethylamino group which is substituted with 1 to 3 fluorine atoms at the 2-position.

2. The peptide according to claim 1 wherein Z is ethylamino group or 2-fluoroethylamino group.

3. N-Acetyl-N-methylglycyl-L-histidyl-L-tryptophyl-L-seryl-L-tyrosyl-D-alanyl-L-leucyl-L-arginyl-L-proline-ethylamide.

4. N-Acetyl-N-methylglycyl-L-histidyl-L-tryptophyl-L-seryl-L-tyrosyl-D-alanyl-L-leucyl-L-arginyl-L-proline-2,2,2-trifluoroethylamide.

5. N-Acetyl-N-methylglycyl-L-histidyl-L-tryptophyl-L-seryl-L-tyrosyl-D-norleucyl-L-leucyl-L-arginyl-L-prolineethylamide.

6. N-Acetyl-N-methylglycyl-L-histidyl-L-tryptophyl-L-seryl-L-tyrosyl-D-norleucyl-L-leucyl-L-arginyl-L-proline-β-fluoroethylamide.

7. N-Acetyl-N-methylglycyl-L-histidyl-L-tryptophyl-L-seryl-L-tyrosyl-D-norleucyl-L-leucyl-L-arginyl-L-proline-2,2,2-trifluoroethylamide.

8. A process for preparing a peptide having the formula N-Acetyl-N-methylglycyl-L-histidyl-L-tryptophyl-L-seryl-L-tyrosyl-Y-L-leucyl-L-arginyl-L-prolyl-Z wherein Y is D-αDα-alkylglycine residue of the formula

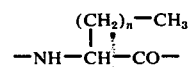

in which n is an integer of 0 through 3 inclusive and Z is ethylamino group or an ethylamino group which is substituted with 1 to 3 fluorine atoms at the 2-position which comprises reacting L-histidyl-L-tryptophyl-L-seryl-L-tyrosyl-Y-L-leucyl-L-arginyl-L-prolyl-Z wherein Y and Z are as defined above with a reactive ester of N-acetyl-N-methylglycine.

* * * * *